Figure 1:
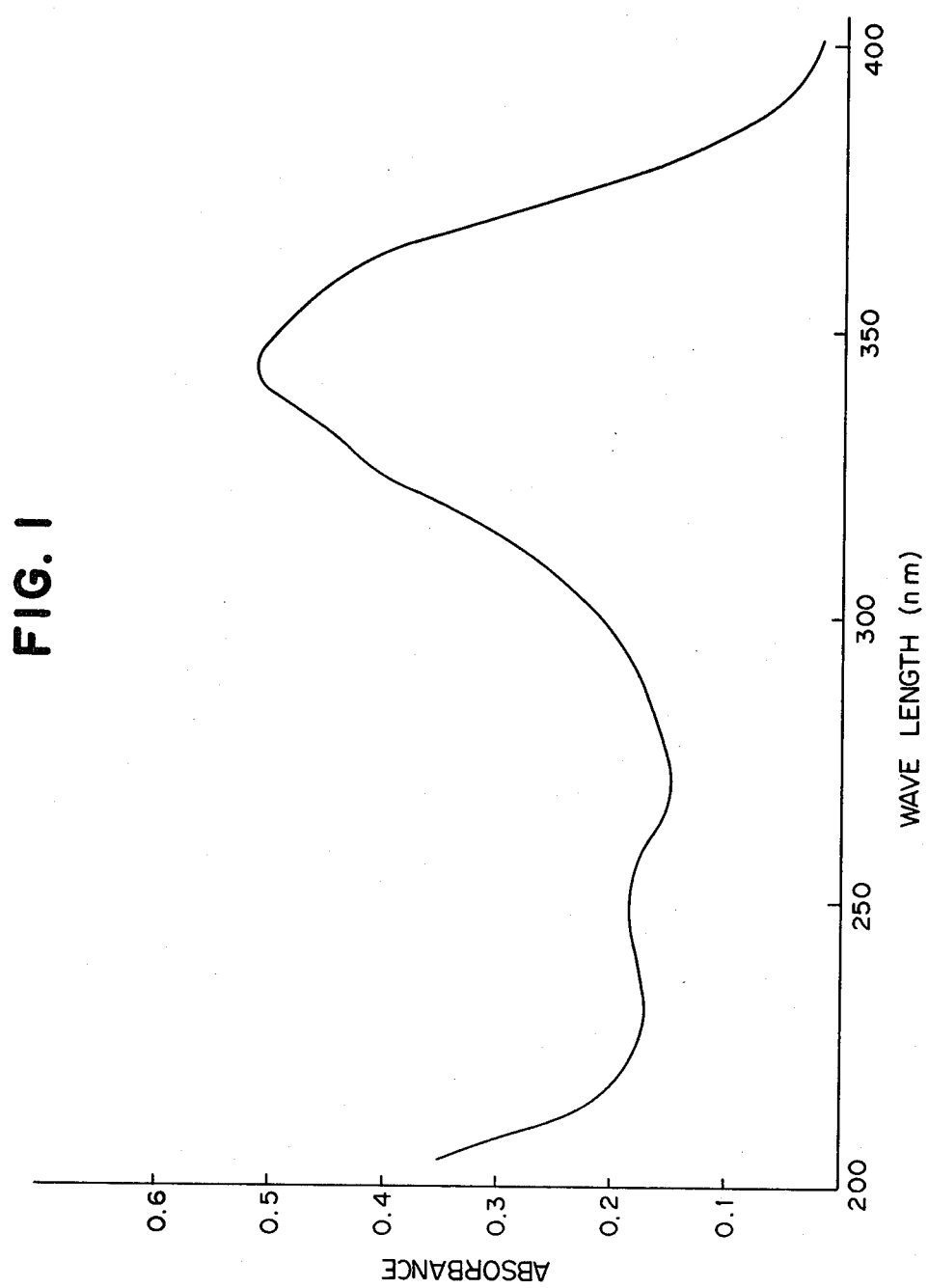

United States Patent [19]

Ezaki et al.

[11] 4,396,603
[45] Aug. 2, 1983

[54] NOVEL ANTIBIOTIC SF-2107 SERIES SUBSTANCE AND PROCESS FOR PREPARING THE SAME

[75] Inventors: Norio Ezaki; Takashi Shomura, both of Yokohama; Shoichi Amano, Kawasaki; Tomizo Niwa, Yokohama; Michio Kojima, Tokyo; Tatsuo Ito, Isehara, all of Japan

[73] Assignee: Meiji Seika Kaisha Ltd., Tokyo, Japan

[21] Appl. No.: 313,370

[22] Filed: Oct. 21, 1981

Related U.S. Application Data

[63] Continuation-in-part of Ser. No. 244,784, Mar. 17, 1981, abandoned.

[30] Foreign Application Priority Data

Apr. 1, 1980 [JP] Japan ................................. 55-41206
Feb. 6, 1981 [JP] Japan ............................... 56-155981

[51] Int. Cl.$^3$ ....................... A61K 35/00; C12P 1/02
[52] U.S. Cl. .................................... 424/118; 424/119; 424/120; 435/171
[58] Field of Search ...................... 424/118, 119, 120; 435/171

Primary Examiner—Jerome D. Goldberg
Attorney, Agent, or Firm—Frishauf, Holtz, Goodman & Woodward

[57] ABSTRACT

Disclosed is a novel antibiotic SF-2107 series substance consisting essentially of Substance SF-2107 A-1, Substance SF-2107 B and/or Substance SF-2107 C, each having the phisico-chemical properties as described in the specification, which substance exhibits an antibacterial activity against both gram-positive and gram-negative bacteria and is useful for pharmaceuticals, bactericides, disinfectants, etc. Also disclosed is a process for preparing the substance.

7 Claims, 6 Drawing Figures

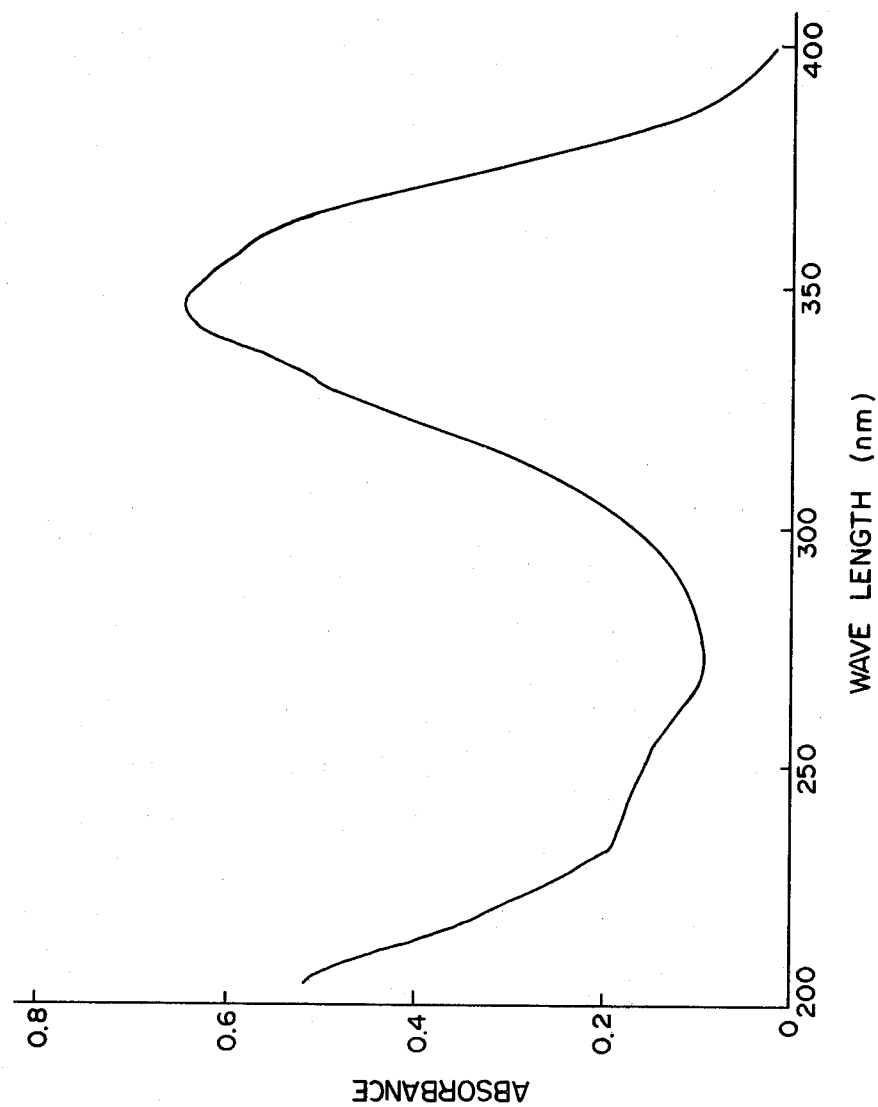

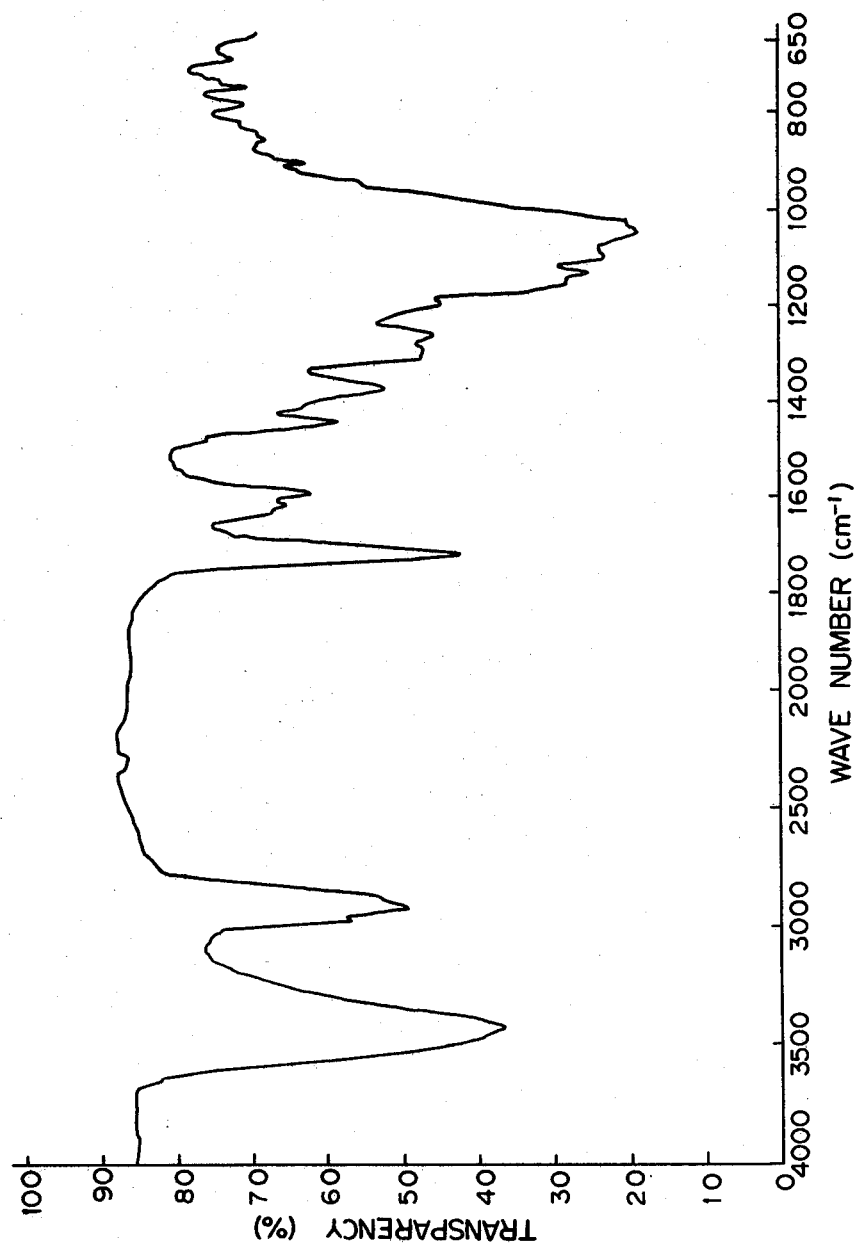

| | |
|---|---|
| Yeast extract (Difco Co., Ltd.): | 1 g |
| Calcium carbonate: | 0.2 g |
| Agar (Difco Co., Ltd.): | 15 g |
| Distilled water: | 1000 ml |

V. CELL WALL COMPOSITION

As a result from analysis according to Becker et al method [See Appln. Microbiol., 13:236 (1965)], the diaminopimelic acid in the cell wall components was mainly of a hydroxy type.

From the foregoing properties, SF-2107 strain has been identified as a strain belonging to the genus Dactylosporangium.

The present inventors have named the SF-2107 strain as Dactylosporangium sp. SF-2107.

This strain has been deposited with Fermentation Research Institute, Agency of Industrial Science & Technology, Ministry of International Trade & Industry, Japan and its accession number of an application in the Fermentation Research Institute is FERM No. 5351. The corresponding strain has also been deposited with American Type Culture Collection under accession number of ATCC No. 31744. The former was deposited on Apr. 1, 1980 and the latter on Nov. 6, 1980.

The SF-2107 strain is apt to have its variable properties as can be seen in the case of many strains in actinomycetes and may be variable by artificial variation procedures, for example, using an ultraviolet ray, an X-ray, a radiation, a chemical agent and the like. However, even any variants are usable in the present process which are capable of producing the SF-2107 series substance and belong to the genus of Dactylosporangium.

In the process according to the present invention, the aforesaid strain can be cultivated on a culture medium containing those nutrients utilizable by ordinary microorganisms. As a nutrient source, there may be employed any materials hitherto well-known to be utilized for the cultivation of actinomycetes. For instance, there may be employed as a carbon source glucose, glycerol, sucrose, starch, dextrin, starch syrup, molasses, soybean oil etc. On the other hand, there may be employed as a nitrogen source soybean meal, wheat embryo, meat extract, peptone, yeast extract, dry yeast, corn steep liquor, cotton seed cake, fish meal, ammonium sulfate, sodium nitrate, urea etc. Additionally, there may be added inorganic salts such as calcium carbonate, sodium chloride, cobalt chloride, phosphates etc., if necessary, and, further, organic and inorganic substances may be suitably incorporated which can promote the growth of a strain and the production of the SF-2107 series substance.

For cultivation, there may be any of cultivation methods under aerobic conditions similarly to the method for the production of general antibiotic substances, but submerged culture is most preferable. Suitable cultivation temperature may be 25°–37° C., but it is preferable in many instances to conduct the cultivation around 28° C.–32° C. Maximum accumulation can be accomplished in 3–10 days in the production of the SF-2107 series substance by either shaken culture or tank culture.

In assay of the SF-2107 series substance, there is used a biological assay with *Vibrio percolans* ATCC 8461. According to this assay, the SF-2107 series substance shows a linear relationship between its logarithmic concentration between its inhibition zone size at 1000 mcg/ml–31.3 mcg/ml, while inhibition circle diameters of 26–14 mm can be seen, respectively, according to a paper disc method.

The SF-2107 series substance has the under-mentioned physico-chemical properties and, accordingly, can be extracted and purified upon such properties, but more effective extraction and purification is feasible according to the procedures as shown below. Namely, the active component which is involved mainly in a solid portion obtained after removal of a liquid portion from a cultured broth by filtration, can be extracted from the solid portion with aqueous acetone, aqueous methanol and the like and, after the organic solvent is distilled off, extracted with a solvent such as ethyl acetate and the like. In the case where the active component is also contained in the filtrate, it may be extracted from a culture filtrate with a solvent such as ethyl acetate and the like. Thereafter, the solvent, e.g., ethyl acetate layer containing the active component is concentrated to dryness and then a pure form of the SF-2107 series substance can be obtained by any suitable combination of chromatography using as a support silica gel, alumina, Sephadex LH-20 (Pharmacia Fine Chemicals), Florisil and so on and a counter-current distribution method. The SF-2107 series substance thus obtained can develop a single spot on all of thin-layer chromatography using various solvent systems and thus can be regarded as a pure form.

Figure 2:
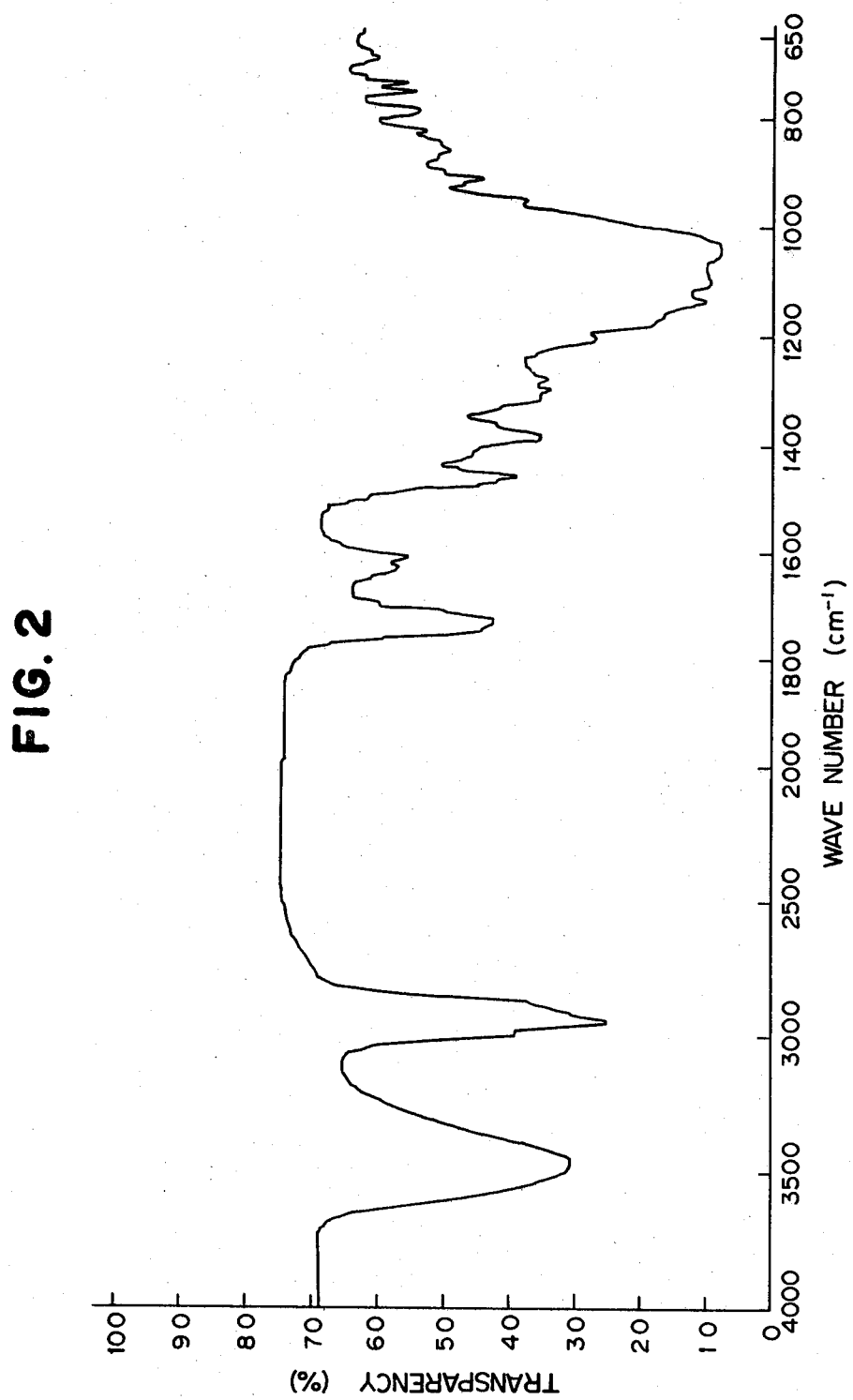
Figure 3:
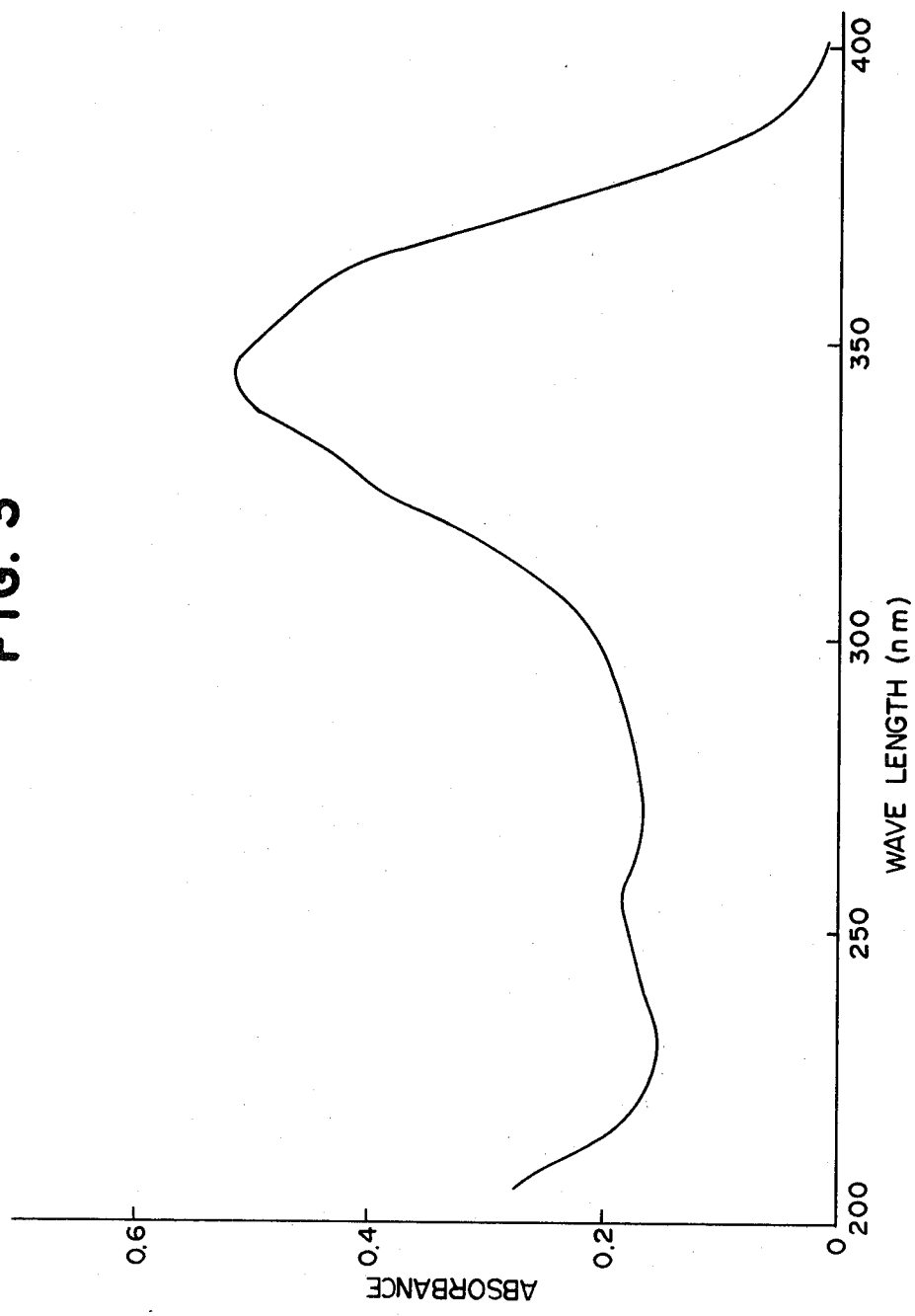
Figure 4:
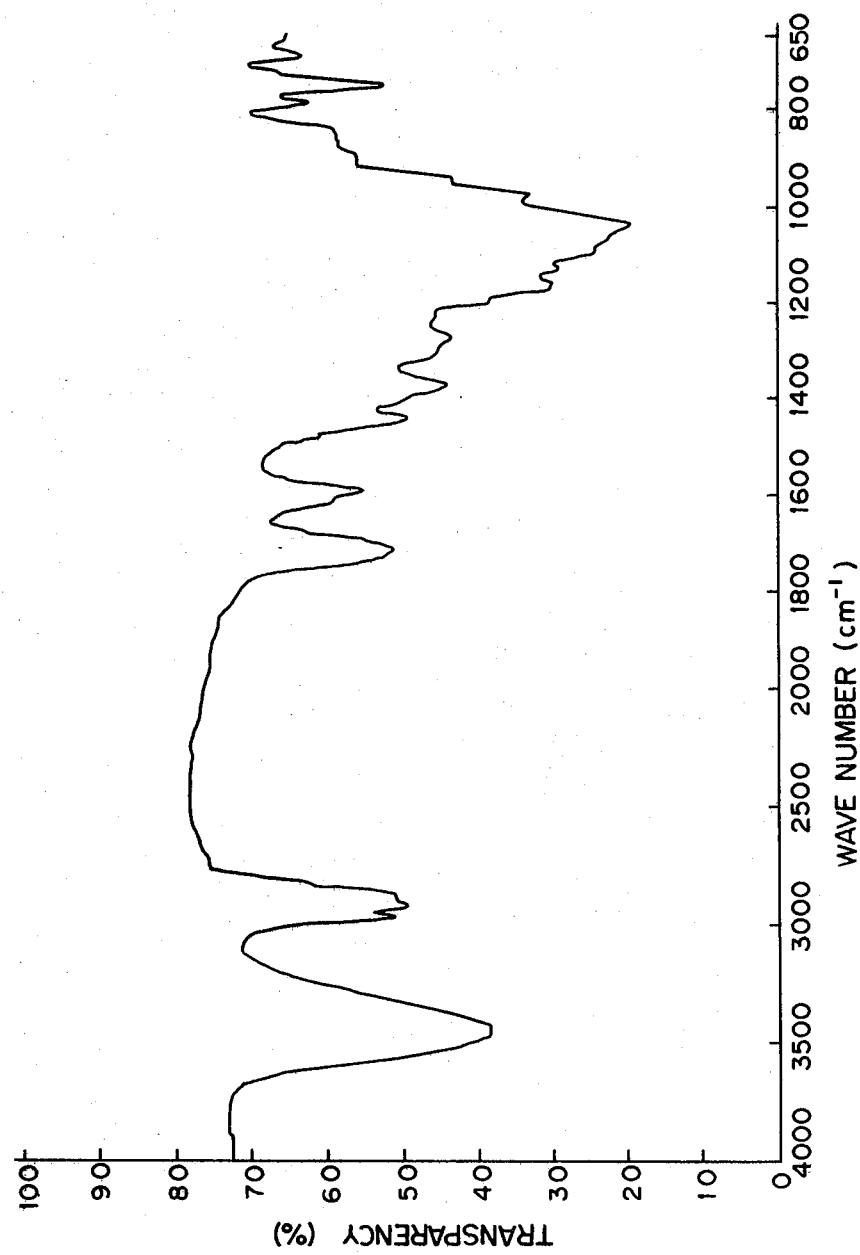

Physico-chemical properties of the SF-2107 series substance obtained according to the above-mentioned procedures are as follows; FIGS. 1, 3 and 5 referred to therein show each an ultraviolet absorption spectrum of the Substance SF-2107 A-1, Substance SF-2107 B and Substance SF-2107 C, respectively, as measured with a methanolic solution of 25 mcg/ml; FIGS. 2, 4 and 6 also referred to therein show each an infrared absorption spectrum of the Substance SF-2107 A-1, Substance SF-2107 B and Substance SF-2107 C, respectively, as measured in a potassium bromide tablet:

I. SUBSTANCE SF-2107 A-1

Elementary analysis:
  C, 58.39 wt %; H, 7.88 wt %; O, 33.73 wt % (balance) which does not contain any nitrogen, sulfur, phosphorus, or halogen.
Molecular weight:
  900–1100 (gel filtration method)
Melting point:
  170°–184° C. (slowly molten)
Specific rotation:
  $[\alpha]_D^{25} = +20°$ (c=0.2, Methanol)
Ultraviolet absorption spectrum:
  Absorption maxima at 250 nm ($E_{1\ cm}^{1\%}=72$), 342 nm (206), (in methanol)
Infrared absorption spectrum:
  Characteristic absorption bands at 3460, 2950, 1730, 1630, 1610, 1460, 1380, 1300, 1280, 1130, 1100, 1040, 910, 860, 820, 790, 750, 740, 690 cm$^{-1}$ (KBr tablet method)
Color reaction:
  Iodine reaction, Lemieux reaction, positive Ninhydrin reaction, ferric chloride reaction, negative
State:
  Pale yellow powder
Neutrality, acidity or basicity:
  Acting as a neutral or weakly acidic substance (electrophoresis)
Silica gel thin-layer chromatography:

NOVEL ANTIBIOTIC SF-2107 SERIES SUBSTANCE AND PROCESS FOR PREPARING THE SAME

This application is a continuation-in-part of our application Ser. No. 244,784, filed Mar. 17, 1981, now abandoned.

This invention relates to a novel antibiotic substance and a process for preparing the same. More particularly, it is concerned with a novel antibiotic SF-2107 series substance, and also with a process for preparing a novel antibiotic SF-2107 series substance which comprises cultivating an antibiotic SF-2107 series substance-producing microorganism belonging to the genus of Dactylosporangium on a culture medium and isolating said antibiotic SF-2107 series substance from the resulting cultured broth.

In this application, the above-mentioned "an antibiotic SF-2107 series substance" means a Substance SF-2107 A-1, Substance SF-2107 B and/or a Substance SF-2107 C.

The present inventors have found that there is produced in the cultured broth of a certain strain a substance which exhibits an antibacterial activity against both gram-positive and gram-negative bacteria. Then, they have isolated said active substance in a pure state and investigated its properties and, as a result, confirmed that it is a novel antibiotic substance different from known substances. This active substance has been named an antibiotic SF-2107 series substance, and more particularly, Substance SF-2107 -1, Substance SF-2107 B or Substance SF-2107 C.

As the new antibiotic SF-2107 series substance-producing microorganism, there may be employed any of those having an ability to produce a sufficient amount of the SF-2107 series substance to be isolated in a cultured broth, but, as an example of these strains, there may be mentioned the SF-2107 strain that was first isolated by the present inventors from a sample of soil collected at Jorinji Temple in Komaoka-cho, Tsurumi-ku, Yokohama-shi, Kanagawa-ken, Japan. Morphological properties of this strain are as recited below.

I. MORPHOLOGICAL CHARACTERISTICS

The substrate mycelium is well-branched, wavy-elongated and of a diameter of about 0.5–0.6μ. No branched substrate mycelia are usually observed on either agar media or liquid media.

Aerial mycelia are hardly observed and appear not to be substantially formed. The SF-2107 strain forms one or tufty sporangium over the surface of agar medium. Many sporangia can be observed on starch agar medium, glycerol. asparagene agar medium and the like. The sporangium is of a finger-shape and of a size of about 0.8–1.1×2.5–4.0μ. Each sporangium contains therein 3–4 spores in a line. When the surface portion of agar medium containing sporangia are scratched off, suspended in a sterile water, allowed to stand for not less than 30 minutes and then viewed under the microscope, it can be observed that the spores show an active motility. When such spores are viewed under the electron microscope, the spores are elliptical or short cylindrical and their surface is smooth and several flagella are observed on their one end.

II. CULTURAL CHARACTERISTICS ON VARIOUS CULTURE MEDIA

Cultural characteristics of the SF-2107 strain on various culture media are as shown in the following Table. As the standard for the symbols shown in the square bracket [] with respect to color indication was employed the color chip number as taught in "Color Harmony Manual", available from Container Corporation of America. Observation was effected after cultivation at 28° C. for 14–21 days.

| Medium | Growth and Color | Sporangium | Aerial mycelium | Soluble pigment |
|---|---|---|---|---|
| Sucrose · nitrate agar | Thin, very poor, colorless | Scant | None | None |
| Glucose · asparagine agar | Very poor, colorless | Abundant | " | " |
| Glycerol · asparagine agar | Poor, colorless | Abundant | " | " |
| Starch agar | Poor, colorless to pale rose beige [4ec] | Abundant | " | " |
| Oatmeal agar | Poor, colorless to very pale yellow | Abundant | " | " |
| Yeast malt agar | Moderate, amber to pale orange [3lc] | None | " | " |
| Tyrosine agar | Moderate, melon yellow [3ga~3ea] | Abundant | " | " |
| Nutrient agar | Poor, colorless | None | " | " |
| BENNETT's agar | Moderate, melon yellow to amber [3ea] | " | " | " |
| Malic acid calcium agar | Very poor, colorless | Scant | " | " |

III. PHYSIOLOGICAL PROPERTIES (1) Growth temperature range: Growth on a yeast-.malt.agar medium at a temperature range of 20°–42° C., good growth at 28°–37° C.

(2) Liquefaction of gelatin: Negative (20° C., cultivated for 21 days)

(3) Hydrolysis of starch: Negative (28° C., cultivated for 14 days)

(4) Nitrate reduction: Positive (28° C., cultivated for 14 days)

(5) Milk peptonization: Negative (28° C., 37° C., cultivated for 14 days) Milk coagulation: Negative (28° C., 37° C., cultivated for 14 days)

(6) Halotolerance: Growth at 1.5%, but no growth at not less than 3.0%

(7) Melanin formation: Negative

| IV. Carbon source utilization: | |
|---|---|
| Carbon source | Growth |
| D-glucose | ++ |
| D-xylose | + |
| D-fructose | ++ |
| D-mannitol | + |
| L-arabinose | + |
| L-rhamnose | + |
| i-inositol | + |
| sucrose | ++ |
| raffinose | + |
| glycerol | + |
| none | + |

++ Good growth (utilization: +)
+ Minor growth (utilization: −)

The basal medium employed:

Rf=0.67 (chloroform:methanol=5:1)=0.56 (acetone:benzene=5:1)

Solubility:
Soluble in methanol, acetone. Sparingly soluble in benzene, chloroform, n-hexane, water

II. SUBSTANCE SF-2107 B

Elementary analysis:
C, 53.66 wt %; H, 6.75 wt %; O, 39.59 wt % (balance) which does not contain any nitrogen, sulfur, phosphorus, or halogen Molecular weight:
900–1100 (gel filtration method)

Melting point:
170°–175° C. (slowly molten)

Specific rotation:
$[\alpha]_D^{23} = -5°$ (c=1, Methanol)

Ultraviolet absorption spectrum:
Absorption maxima at 242 nm ($E_1{}_{cm}^{1\%}=52$), 343 (206), (in methanol)

Infrared absorption spectrum:
Characteristic absorption bands at 3450, 2970, 2930, 1720, 1600, 1440, 1370, 1270, 1170, 1130, 1040, 980, 790, 750, 690 cm$^{-1}$ (KBr tablet method)

Color reaction:
Iodine reaction, Lemieux reaction, positive Ninhydrin reaction, ferric chloride reaction, negative State:
Slightly yellowish powder Neutrality, acidity or basicity:
Acting as a neutral or weakly acidic substance (electrophoresis)

Silica gel thin-layer chromatography:
Rf=0.34 (chloroform:methanol=5:1)=0.51 (acetone:benzene=5:1)

Solubility:
Soluble in methanol, acetone. Sparingly soluble in benzene, chloroform, n-hexane, water

III. SUBSTANCE SF-2107 C

Elementary analysis:
C, 57.50 wt %; H, 7.04 wt %; O, 35.46 wt % (balance) which does not contain any nitrogen, sulfur, phosphorus, or halogen.

Molecular weight:
900–1100 (gel filtration method)

Melting point:
155°–168° C. (slowly molten)

Specific rotation:
$[\alpha]_D^{23} = +29.8°$ (c=1, methanol)

Ultraviolet absorption spectrum:
Absorption maximum at 345 nm ($E_1{}_{cm}^{1\%}=258$) (in methanol)

Infrared absorption spectrum:
Characteristic absorption bands at 3430, 2930, 1720, 1620, 1600, 1440, 1370, 1300, 1270, 1130, 1100, 1050, 900, 790, 750, 690 cm$^{-1}$ (KBr tablet method)

Color reaction:
Iodine reaction, Lemieux reaction, positive Ninhydrin reaction, ferric chloride reaction, negative State:
Slightly yellowish powder Neutrality, acidity or basicity:
Acting as a neutral or weakly acidic substance (electrophoresis)

Silica gel thin-layer chromatography:
Rf=0.27 (chloroform:methanol=5:1)=0.07 (acetone:benzene=5:1)

Solubility:
Soluble in methanol, acetone. Sparingly soluble in benzene, chloroform, n-hexane, water Minimum inhibitory concentrations (MIC) against various bacteria of the SF-2107 series substance as assayed by an agar dilution method are given in the following Table 1, which demonstrates effectiveness against both gram-positive and gram-negative bacteria. Also, acute toxicity tests of the present substance in mice showed that all animals survived at 90 mg/kg via intraperitoneal administration. Accordingly, the antibiotic SF-2107 series substance is useful for pharmaceuticals, drugs for animals, bactericides, and disinfectants, as well as for convertion materials thereto.

As the pharmaceuticals for which the antibiotic SF-2107 series substance or a salt thereof is useful, there may be mentioned various types for oral, topical or parenteral administrations such as tablets, capsules, creams, syrup, suspensions, solutions, powders and sterilized compositions suitable for injections or the like. The pharmaceuticals according to the present invention may be administered at the dosage of 30 to 50 mg a day, more generally, 3 to 300 mg a day.

Comparison was effected in physico-chemical properties and biological activities between the SF-2107 series substance and known antibiotic substances, by which it has been proven that there are no corresponding known substances, and, therefore, the present substance has been evident to be a novel antibiotic substance.

Examples are given below for the production of the SF-2107 series substance, but it is to be noted that many other variation and modification means not illustrated herein may be applied.

TABLE 1

| Test Organism | MIC (mcg/ml) SF-2107 | | |
|---|---|---|---|
| | A-1 | B | C |
| Staphyloccus aureus JC-1 | 3.13 | 25 | 0.78 |
| Staphylococcus epidermidis ATCC 14900 | 3.13 | 50 | 6.25 |
| Bacillus anthracis No 119 | 0.78 | 12.5 | 0.39 |
| Escherichia coli JC-2 | >100 | >100 | >100 |
| Escherichia coli RGN 823 | 0.78 | 50 | 6.25 |
| Salmonella typhi D-901-W | 25 | >100 | >100 |
| Klebsiella pneumoniae PCI 602 | >100 | >100 | >100 |
| Proteus vulgaris OX 19 | 6.25 | 50 | 6.25 |
| Serratia marcescens MB-3838 | 25 | >100 | >100 |
| Pseudomonas cepacia M-0527 | 3.13 | 50 | 6.25 |
| Pseudomonas maltophilia M-0627 | 0.20 | 100 | 6.25 |

Midium: Heart infusion agar (Eiken Chemical Ltd.)

EXAMPLE 1

As a seed culture, there was used Dactylosporangium sp. SF-2107 strain (FERM. No. 5351 or ATCC No. 31744) and, as a seed culture medium, a medium containing glucose 1.0%, soluble starch 1.0%, Polypepton 0.5%, meat extract 0.2%, yeast extract 0.3%, soybean meal 0.2% and calcium carbonate 0.2% (pH 7.0 before sterilization).

Six to 7 platinum loops of the seed culture, which had been cultivated on a yeast-malt-agar slant medium at 28° C. for 14 days, were inoculated into 20 ml of the above-mentioned seed culture medium in a 100 ml volume Erlenmeyer flask and then shaken culture was effected at 28° C. for 6 days. This was used as the first seed culture and three flasks were cultivated.

Subsequently, this seed culture was inoculated into 80 ml of the seed culture medium in each of six 500 ml volume Erlenmeyer flasks in 8 ml portions and then shaken culture was effected at 28° C. for 3 days. This was used as the second seed culture.

In each of the one hundred 500 ml volume Erlenmeyer flasks were placed 80 ml of a production medium, into which the above-mentioned second seed culture was then inoculated at a rate of 5%.

As the production medium, there was employed a culture medium having the composition of glucose 2.5%, wheat embryo 2.0%, Sungrain (manufactured by Suntory Ltd.) 0.5%, and sodium chloride 0.25% (pH 7.0 before sterilization).

Cultivation was effected by shaken culture at 28° C. for 7 days by means of a rotary shaker (220 rpm). After completion of the cultivation, filtration was done to remove the filtrate, 6 l of 80% acetone in water were added to the resulting solid and then stirring was effected to extract the Substance SF-2107 A-1. The acetone was distilled off under reduced pressure from the extract, the residue was dissolved in water to 1.3 l of an aqueous solution, the pH of the resulting solution adjusted to 9 and extraction was made twice with 1 l portions of ethyl acetate. The extracts were combined, concentrated to dryness under reduced pressure to afford 300 mg of an oily substance. This was dissolved in 3 ml of methanol, applied to a column packed with 100 ml of Sephadex LH-20 (Farmacia Fine Chemicals) and developed with methanol to separate active fractions, which were then concentrated under reduced pressure and dried to give 120 mg of a powdery substance. The resulting powdery substance was applied to a column packed with 20 ml of Wako Gel C-200 (Wako Pure Chemical Industries Ltd.), which was developed with a mixed solvent of chloroform-methanol (50:1). Of the active fractions, those fractions showing a single spot in a thin-layer chromatography were concentrated to dryness to afford 16 mg of a pale yellow powder of the Substance SF-2107 A-1.

EXAMPLE 2

As a seed culture, there was used Dactylosporangium sp. SF-2107 strain (FERM No. 5351 or ATCC No. 31744) and, as a seed culture medium, a medium containing soluble starch 2.0%, glucose 1.0%, wheat embryo 0.6%, soybean meal 0.2%, Polypepton 0.5%, yeast extract 0.3%, meat extract 0.2% and calcium carbonate 0.1% (pH 7.0 before sterilization).

Five platinum loops of the seed culture, which had been cultivated on a yeast-malt-agar slant medium at 28° C. for 14 days, were inoculated into 20 ml of the above-mentioned seed culture medium in a 100 ml volume Erlenmeyer flask and then shaken culture was effected at 32° C. for 96 hours. This was used as the first seed culture. Subsequently, this seed culture broth was inoculated in 8 ml portions into 80 ml of the seed culture medium in each of ten 500 ml volume Erlenmeyer flasks and then shaken culture was effected at 32° C. for 72 hours. This was used as the second seed culture.

In a 30 l volume jar fermenter were placed 20 l of a production medium and 800 ml of the above-mentioned second seed culture were inoculated thereinto. As the production medium, there was used a medium having the composition of glucose 1.7%, sucrose 1.5%, wheat embryo 2.0%, yeast extract 0.2%, gluten meal 0.3%, and sodium chloride 0.25% (pH 7.0 before sterilization).

Cultivation was effected by aerated agitation culture at 28° C. for 164 hours. After completion of the cultivation, filtration was done to remove the filtrate, 12 l of 80% acetone in water were added to a solid and stirring was made to extract an active ingredient. The acetone was distilled off under reduced pressure, the residue dissolved in water to 2 l of an aqueous solution, which was then adjusted to pH 9 and extracted twice with 1.5 l portions of ethyl acetate. The extracts were combined and concentrated to dryness under reduced pressure to yield 800 mg of an oily substance. This was dissolved in 5 ml of methanol and applied to a column packed with 500 ml of Sephadex LH-20 (Pharmacia Fine Chemicals), which was then developed with methanol to separate active fractions. These fractions were concentrated to dryness to afford 280 mg of a powdery substance.

This powdery substance was applied to a column packed with 100 ml of Wako Gel C-200 (Wako Pure Chemical Industries Ltd.), which was developed stepwise, first with 1000 ml of a mixed solvent of chloroform-methanol (25:1) and then with 2000 ml of a mixed solvent of chloroform-methanol (15:1) to collect 20 ml each of fractions by using a fraction collector. Active fractions were found at Fraction Nos. 41–65, Nos. 76–89 and Nos. 95–120.

The active fractions thus obtained were subjected to silica gel thin-layer chromatography using the solvent system (I) of chloroform-methanol (5:1) and the solvent system (II) of acetone-benzene (5:1). The fraction showing RF=0.67 with the system (I) and the fraction showing RF=0.56 with the system (II) were combined and concentrated to dryness under reduced pressure to give 60 mg of powdery Substance SF-2107 A-1. The fraction showing RF=0.34 with the system (I) and the fraction of Rf=0.51 with the system (II) were combined and concentrated to dryness under reduced pressure to give 52 mg of Substance SF-2107 B. Further, the fraction showing Rf=0.27 with the system (I) and the fraction showing Rf=0.07 with the system (II) were combined and concentrated to dryness under reduced pressure to give 93 mg of Substance SF-2107 C.

EXAMPLE 2-1

60 mg of the powdery Substance SF-2107 A-1 obtained according to Example 2 was dissolved in methanol to a concentration of about 2% and fractionated by a high performance liquid chromatography, using a column of Micropondapak C 18 (Waters Co.) and, as an eluant, a mixed solvent of methanol-acetonitrile-water (7:1:3). The resulting fractions were concentrated to dryness under reduced pressure to give 36 mg of a pale yellow powder of pure substance of the Substance SF-2107 A-1.

EXAMPLE 2-2

52 mg of the Substance SF-2107 B and 93 mg of the Substance SF-2107 C obtained according to Example 2 were respectively dissolved in a small amount of methanol, and applied separately to a column packed with 50 ml of Sephadex LH-20 (Pharmacia Fine Chemicals), which were then developed with methanol. The active fractions were subjected to thin-layer chromatography using the aforementioned two solvent systems, and the fractions showing a single spot therein were combined and concentrated to dryness under reduced pressure to yield 38 mg of pure substance of the Substance SF-2107

B and 76 mg of pure substance of the Substance SF-2107 C, respectively.

EXPERIMENT 1

Therapeutic effect of SF-2107 series substance on mice infected with *Pseudomonas cepacia*

(a) Sample: Substance SF-2107 A-1

(b) Host animals: ddY-SLC female mice of average body weight of 19 g of 4-week age, each group consisting of 3 animals.

(c) Test strain: *Pseudomonas cepacia* M-0527. The strain was cultured to prepare solutions containing the *Pseudomonas cepacia*.

(d) Dose and administration of the sample: The samples were dissolved in ethanol and adjusted with sterilized physiological saline solution to form solution of given concentrations (ethanol concentration: 10%), which were administered orally and subcutaneously at 2 dose levels, respectively: 10 mg/mouse and 1 mg/mouse in oral administration; 5 mg/mouse and 1 mg/mouse in subcutaneous administration. The dose volumes were 0.5 ml/mouse in the oral administration and 0.2 ml/mouse in the subcutaneous administration.

(e) Test procedures: Solutions containing the *Pseudomonas cepacia* were inoculated into abdominal cavities of the respective mice (inoculated bacterial number: $6.75 \times 10^7$ cells/mouse, MLD). Immediately thereafter, the sample solutions were administered orally, or subcutaneously at the femurs, at the dosage as prescribed above to observe the living bodies after 7 days.

(f) Test results: As seen from the following Table, the Substance SF-2107 A-1 showed excellent therapeutic effect on mice infected with *Pseudomonas cepacia*.

|  | Living bodies after 7 days | | | | |
|---|---|---|---|---|---|
|  | Oral administration | | Subcutaneous administration | | Control |
| Dose (mg/mouse) | 10 | 1 | 5 | 1 |  |
| Living bodies | 3 | 2 | 3 | 2 | 0 |

(3 mice for each group)

We claim:

1. An antibiotic Substance SF-2107 A-1 having the following physico-chemical properties:

Elementary analysis:
  C, 58.39 wt %; H, 7.88 wt %; O, 33.73 wt % (balance) which does not contain any nitrogen, halogen, sulfur, phosphorus Molecular weight:
  900-1100 (gel filtration method)

Melting point:
  170°-184° C. (slowly molten)

Specific rotation:
  $[\alpha]_D^{25} + 20°$ (c=0.2, Methanol)

Ultraviolet absorption spectrum:
  Absorption maxima at 250 nm ($E_{1\ cm}^{1\%}=72$), 342 nm (206), (in methanol)

Infrared absorption spectrum:
  Characteristic absorption bands at 3460, 2950, 1730, 1630, 1610, 1460, 1380, 1300, 1280, 1130, 1100, 1040, 910, 860, 820, 790, 750, 740, 690 cm$^{-1}$ (KBr tablet method)

Color reaction:
  Iodine reaction, Lemieux reaction, positive Ninhydrin reaction, ferric chloride reaction, negative State:
  Pale yellow powder Neutrality, acidity or basicity:
  Acting as a neutral or weakly acidic substance (electrophoresis)

Silica gel thin-layer chromatography:
  Rf=0.67 (chloroform:methanol=5:1)=0.56 (acetone:benzene=5:1)

Solubility:
  Soluble in methanol, acetone. Sparingly soluble in benzene, chloroform, n-hexane, water 2. An antibiotic Substance SF-2107 B having the following physico-chemical properties:

Elementary analysis:
  C, 53.66 wt %; H, 6.75 wt %; O, 39.59 wt % (balance) which does not contain any nitrogen, sulfur, phosphorus, or halogen Molecular weight:
  900-1100 (gel filtration method)

Melting point:
  170°-175° C. (slowly molten)

Specific rotation:
  $[\alpha]_D^{23} = -5°$ (c=1, Methanol)

Ultraviolet absorption spectrum:
  Absorption maxima at 242 nm ($E_{1\ cm}^{1\%}=52$), 343 (206), (in methanol)

Infrared absorption spectrum:
  Characteristic absorption bands at 3450, 2970, 2930, 1720, 1600, 1440, 1370, 1270, 1170, 1130, 1040, 980, 790, 750, 690 cm$^{-1}$ (KBr tablet method)

Color reaction:
  Iodine reaction, Lemieux reaction, positive Ninhydrin reaction, ferric chloride reaction, negative State:
  Slightly yellowish powder Neutrality, acidity or basicity:
  Acting as a neutral or weakly acidic substance (electrophoresis)

Silica gel thin-layer chromatography:
  Rf=0.34 (chloroform:methanol=5:1)=0.51 (acetone:benzene=5:1)

Solubility:
  Soluble in methanol, acetone. Sparingly soluble in benzene, chloroform, n-hexane, water 3. An antibiotic Substance SF-2107 C having the following physico-chemical properties:

Elementary analysis:
  C, 57.50 wt %; H, 7.04 wt %; O, 34.46 wt % (balance) which does not contain any nitrogen, sulfur, phosphorus, or halogen Molecular weight:
  900-1100 (gel filtration method)

Melting point:
  155°-168° C. (slowly molten)

Specific rotation:
  $[\alpha]_D^{23} = +29.8°$ (c=1, methanol)

Ultraviolet absorption spectrum:
  Absorption maximum at 345 nm ($E_{1\ cm}^{1\%}=258$) (in methanol)

Infrared absorption spectrum:
  Characteristic absorption bands at 3430, 2930, 1720, 1620, 1600, 1440, 1370, 1300, 1270, 1130, 1100, 1050, 900, 790, 750, 690 cm$^{-1}$ (KBr tablet method)

Color reaction:
  Iodine reaction, Lemieux reaction, positive Ninhydrin reaction, ferric chloride reaction, negative State:
  Slightly yellowish powder Neutrality, acidity or basicity:

Acting as a neutral or weakly acidic substance (electrophoresis)
Silica gel thin-layer chromatography:
Rf=0.27 (chloroform:methanol=5:1)=0.07 (acetone:benzene=5:1)
Solubility:
Soluble in methanol, acetone. Sparingly soluble in benzene, chloroform, n-hexane, water 4. A process for preparing the antibiotic SF-2107 series substances consisting of SF-2107 A-1, SF-2107B and Sf-2107C as defined in claim 1, or 2 or 3 which comprises cultivating antibiotic SF-2107 series substance-producing microorganism Dactylosporangium sp. SF-2107 in a culture broth containing a carbon source and a nitrogen source under aerobic conditions until substantial antibiotic activity is imparted to said broth and at a temperature of between 25° and 37° C. to produce said antibiotic SF-2107 series substance, and isolating from the culture broth said antibiotic SF-2107 series substance.

5. An antibacterial composition which comprises as an active ingredient, an antibacterially effective amount of Substance SF-2107 A-1 having the following physico-chemical properties:
Elementary analysis:
C, 58.39 wt %, H, 7.88 wt %; O, 33.73 wt % (balance) which does not contain any nitrogen, sulfur, phosphorus, or halogen
Molecular weight:
900-1100 (gel filtration method)
Melting point:
170°-184° C. (slowly molten)
Specific rotation:
$[\alpha]_D^{25} = +20°$ (c=0.2, Methanol)
Ultraviolet absorption spectrum:
Absorption maxima at 250 nm ($E_{1\ cm}^{1\%}=72$), 342 nm (206), (in methanol)
Infrared absorption spectrum:
Characteristic absorption bands at 3460, 2950, 1730, 1630, 1610, 1460, 1380, 1300, 1280, 1130, 1100, 1040, 910, 860, 820, 790, 750, 740, 690 cm$^{-1}$ (KBr tablet method)
Color reaction:
Iodine reaction, Lemieux reaction, positive Ninhydrin reaction, ferric chloride reaction, negative
State:
Pale yellow powder
Neutrality, acidity or basicity:
Acting as a neutral or weakly acidic substance (electrophoresis)
Silica gel thin-layer chromatography: Rf=0.67 (chloroform:methanol=5:1)=0.56 (acetone:benzene=5:1)
Solubility:
Soluble in methanol, acetone. Sparingly soluble in benzene, chloroform, n-hexane, water, and a pharmaceutically acceptable carrier.

6. An antibacterial composition which comprises as an active ingredient, an antibacterially effective amount of Substance SF-2107 B having the following physico-chemical properties:
Elementary analysis:
C, 53.66 wt %; H, 6.75 wt %; O, 39.59 wt % (balance) which does not contain any nitrogen, sulfur, phosphorus, or halogen
Molecular weight:
900-1100 (gel filtration method)
Melting point:
170°-175° C. (slowly molten)
Specific rotation:
$[\alpha]_D^{23} = -5°$ (c=1, Methanol)
Ultraviolet absorption spectrum:
Absorption maxima at 242 nm ($E_{1\ cm}^{1\%}=52$), 343 (206), (in methanol)
Infrared absorption spectrum:
Characteristic absorption bands at 3450, 2970, 2930, 1720, 1600, 1440, 1370, 1270, 1170, 1130, 1040, 980, 790, 750, 690 cm$^{-1}$ (KBr tablet method)
Color reaction:
Iodine reaction, Lemieux reaction, positive Ninhydrin reaction, ferric chloride reaction, negative
State:
Slightly yellowish powder
Neutrality, acidity or basicity:
Acting as a neutral or weakly acidic substance (electrophoresis)
Silica gel thin-layer chromatography:
Rf=0.34 (chloroform:methanol=5:1)=0.51 (acetone:benzene=5:1)
Solubility:
Soluble in methanol, acetone. Sparingly soluble in benzene, chloroform, n-hexane, water, and a pharmaceutically acceptable carrier.

7. An antibacterial composition which comprises as an active ingredient, an antibacterially effective amount of Substance SF-2107 C having the following physico-chemical properties:
Elementary analysis:
C, 57.50 wt %; H, 7.04 wt %; O, 35.46 wt % (balance) which does not contain any nitrogen, sulfur, phosphorus, or halogen
Molecular weight:
900-1100 (gel filtration method)
Melting point:
155°-168° C. (slowly molten)
Specific rotation:
$[\alpha]_D^{23} = +29.8°$ (c=1, methanol)
Ultraviolet absorption spectrum:
Absorption maximum at 345 nm ($E_{1\ cm}^{1\%}=258$) (in methanol)
Infrared absorption spectrum:
Characteristic absorption bands at 3430, 2930, 1720, 1620, 1600, 1440, 1370, 1300, 1270, 1130, 1100, 1050, 900, 790, 750, 690 cm$^{-1}$ (KBr tablet method)
Color reaction:
Iodine reaction, Lemieux reaction, positive Ninhydrin reaction, ferric chloride reaction, negative
State:
Slightly yellowish powder
Neutrality, acidity or basicity:
Acting as a neutral or weakly acidic substance (electrophoresis)
Silica gel thin-layer chromatography:
Rf=0.27 (chloroform:methanol=5:1)=0.07 (acetone:benzene=5:1)
Solubility:
Soluble in methanol, acetone. Sparingly soluble in benzene, chloroform, n-hexane, water, and a pharmaceutically acceptable carrier.

* * * * *